(12) United States Patent
Solf (10) Patent No.: US 8,598,534 B2
(45) Date of Patent: Dec. 3, 2013

(54) LOW-POWER TDC-ADC AND ANGER LOGIC IN RADIATION DETECTION APPLICATIONS

(75) Inventor: Torsten Solf, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 489 days.

(21) Appl. No.: 12/920,481

(22) PCT Filed: Feb. 25, 2009

(86) PCT No.: PCT/IB2009/050755
§ 371 (c)(1),
(2), (4) Date: Sep. 1, 2010

(87) PCT Pub. No.: WO2009/112962
PCT Pub. Date: Sep. 17, 2009

(65) Prior Publication Data
US 2011/0001053 A1    Jan. 6, 2011

Related U.S. Application Data

(60) Provisional application No. 61/036,094, filed on Mar. 13, 2008.

(51) Int. Cl.
*G01T 1/24*    (2006.01)

(52) U.S. Cl.
USPC ............... 250/370.08; 250/369; 250/363.02; 250/395; 327/544

(58) Field of Classification Search
USPC ......... 250/369, 363.02, 370.08, 395; 327/544
See application file for complete search history.

(56) References Cited

U.S. PATENT DOCUMENTS 5,309,357 A    5/1994 Stark et al.
7,091,489 B2   8/2006 Schlyer et al.

(Continued)

FOREIGN PATENT DOCUMENTS

| JP | S60144685 A | 7/1985 |
|---|---|---|
| JP | H03233384 A | 10/1991 |
| JP | H11304926 A | 11/1999 |
| JP | 3818317 B1 | 9/2006 |

OTHER PUBLICATIONS

Mäntyniemi, "An Integrated CMOS High Precision Time-to-Digital Converter Based on Stabilized Three-Stage Delay Line Interpolation", University of Oulu, Finland, Dept. of Electrical & Information Eng., pp. 22-23, 2004.
Wong, et al. "Front End Electronics for a Variable Field PET Camera Using the PMT-Quadrant", Nucl. Sci. Symposium, 1996, Conf. Record, 1996 IEEE 2: 1320-1324 Nov. 1996.
Back, T., et al.; A TOF-PET system for educational purposes; 2002; Nuclear Instruments and Methods in Physics Research; A477; 82-87.

*Primary Examiner* — David Porta
*Assistant Examiner* — Djura Malevic (57) ABSTRACT

A diagnostic imaging device includes a signal processing circuit (22) processes signals from a detector array (16) which detects radiation from an imaging region (20). The hit signals are indicative of a corresponding detector (18) being hit by a radiation photon. The signal processing circuit (22) includes a plurality of input channels ($32_1$, $32_2$, $32_3$, $32_4$), each input channel receiving hit signals from a corresponding detector element (18) such that each input channel ($32_1$, $32_2$, $32_3$, $32_4$) corresponds to a location at which each hit signal is received. A plurality of integrators (42) integrate signals from the input channels (32) to determine an energy value associated with each radiation hit. A plurality of analog-to-digital converters ($44_1$, $44_2$, $44_3$, $44_4$) convert the integrated energy value into a digital energy value. A plurality of time to digital converters (40) receive the hit signals and generate a digital time stamp. OR logic (36, 38) relays signal hits from a subset of the plurality of input channels (32) to one of the ADC (44) and one of the time to digital converters (40), the subset including more than one input channel such that more than one input channel is connected with each ADC (44) and/or each time-to-digital converter (40). A register and read out (25) reads out the locations, the digital energy values, and the digital time stamps for hit signals.

19 Claims, 8 Drawing Sheets

(56) References Cited

U.S. PATENT DOCUMENTS

| | | |
|---|---|---|
| 7,132,664 B1 | 11/2006 | Crosetto |
| 7,301,151 B2 | 11/2007 | Rutten et al. |
| 7,750,305 B2 | 7/2010 | Solf et al. |
| 2003/0062482 A1* | 4/2003 | Williams et al. ......... 250/363.03 |
| 2004/0200966 A1 | 10/2004 | Ramsden |
| 2005/0167599 A1* | 8/2005 | Schlyer et al. ........... 250/363.03 |
| 2005/0211893 A1* | 9/2005 | Paschalidis .................... 250/287 |
| 2006/0113479 A1* | 6/2006 | Zavarzin .................. 250/363.03 |
| 2009/0236532 A1* | 9/2009 | Frach et al. .............. 250/363.04 |

\* cited by examiner

LOW-POWER TDC-ADC AND ANGER LOGIC IN RADIATION DETECTION APPLICATIONS

CROSS REFERENCE TO RELATED APPLICATIONS

This application claims the benefit of U.S. Provisional Application Ser. No. 61/036,094 filed Mar. 13, 2008, which is incorporated herein by reference.

The present application relates to the diagnostic imaging arts. It finds particular application in reducing power consumption of electronics associated with detecting radiation, and will be described with particular reference thereto. It is to be understood, however, that it also finds application in reducing the power consumption of arrays of photodetectors, and is not necessarily limited to the aforementioned application.

The use of silicon photo multipliers (SiPM) or multi-anode photomultiplier tubes (PMTs) enable high performance time-of-flight positron emission tomography (ToF-PET) detectors. These detectors have high temporal, spatial, and energy resolutions, and minimize pile up effects due to the relatively small size of the detectors (a few mm). The number of read out channels to accommodate such high density detector arrays increases significantly over classical PMT detectors. Integrated low-power electronics conveniently accommodate the demands, especially for ToF-PET. Also, the use of neighbor logic adds complexity to the electronics. This is especially true if triggering circuitry has to be added based on the components used. This added circuitry often lacks gain and delay matching, so the time stamping operation resultantly suffers.

Current time-to-digital (TDC) and analog-to-digital (ADC) application specific integrated circuit (ASIC) designs perform well. While each one consumes relatively little power, a high density array of them consumes a relatively high amount of power, resulting in having to dissipate approximately 1 W/cm$^2$ of heat. As the analog path from the detector to the digitizers should be as short as possible, the detectors heat up when the electronics associated with the detectors are not cooled properly. In the case of an SiPM readout, the performance of the detectors varies significantly with temperature, so adequate cooling and thermal design is needed, adding cost and complexity to the system.

Traditional multi-channel TDC/ADCs are typically composed of a multiplicity of identical channels each having a timing branch and an energy branch. A radiation event recordation or "hit" is typically produced if the signal exceeds the trigger threshold in the timing branch which then starts the analog integration and conversion in the energy branch. The channel information along with the time stamp and energy information is then sent to a sub-system for further processing and later coincidence search to form lines of response (LORs) which are the basis of PET images. Processors that provide time stamping often use time to amplitude conversion (TAC) which require long conversion times, reference start or stop signals, and long reset times.

Self triggered digitizers (TDC/ADC ASICs) exhibit excellent performance but do not provide a fixed set of information for Anger Logic based pixel identification using a single look-up table (LUT). This is due to the fact that low energy events do not produce triggers if they do not exceed the individual triggering threshold.

The present application provides a new and improved radiation detector array which overcomes the above-referenced problems and others.

In accordance with one aspect, a diagnostic imaging device is provided. A signal processing circuit processes signals from a detector array which detects radiation from an imaging region. The hit signals are indicative of a corresponding detector being hit by a radiation photon. The signal processing circuit includes a plurality of input channels, each input channel receiving hit signals from a corresponding detector element such that each input channel corresponds to a location at which each hit signal is received. A plurality of integrators integrate signals from the input channels to determine an energy value associated with each radiation hit. A plurality of analog-to-digital converters convert the integrated energy value into a digital energy value. A plurality of time to digital converters receive the hit signals and generate a digital time stamp. OR logic relays signal hits from a subset of the plurality of input channels to one of the ADC and one of the time to digital converters, the subset including more than one input channel such that more than one input channel is connected with each ADC and/or each time-to-digital converter. A register and read out reads out the locations, the digital energy values, and the digital time stamps for hit signals.

In accordance with another aspect, a method of diagnostic imaging is provided. Signals from a detector array are processed detecting radiation from an imaging region, the signals being indicative of a corresponding detector being hit by a radiation photon. Hit signals are received from a plurality of input channels, each input channel having a corresponding detector element such that each input channel corresponds to a location at which each hit signal is received. Signals from the input channels are integrated to determine an energy value associated with each radiation hit. The integrated energy value is converted into a digital energy value. The hit signals are received and a digital time stamp is generated. Signal hits are relayed from a subset of the plurality of input channels to one of the ADC and one of the time to digital converters, the subset including more than one input channel such that more than one input channel is connected with each ADC and/or each time-to-digital converter. The locations, the digital energy values, and the digital time stamps are read out for hit signals.

In accordance with another aspect, a method of reducing power consumption of a signal processing circuit which processes hit signals from a detector array which detects radiation from an imaging region, the hit signals being indicative of a corresponding detector being hit by a radiation photon is provided. Hit signals are received with a plurality of input channels from a corresponding detector element such that each input channel corresponds to a location at which each hit signal is received. Signals are integrated from the input channels to determine an energy value associated with each radiation hit. The integrated energy value is converted into a digital energy value. The hit signals are received and a digital time stamp is generated. Power draw is reduced by using OR logic to combine input channels such that more than one input channel is connected with each ADC and/or each time-to-digital converter. The locations, the digital energy values, and the digital time stamps are read out for hit signals.

One advantage is that timing jitter is reduced.

Another advantage lies in reduced dead time of detector elements.

Another advantage lies in reduced heat generation

Another advantage is lower power consumption.

Another advantage lies in simplified circuit layout.

Another advantage lies in increased ease of cooling heat sensitive components.

Another advantage lies in increased ease of supplying power to low voltage devices.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
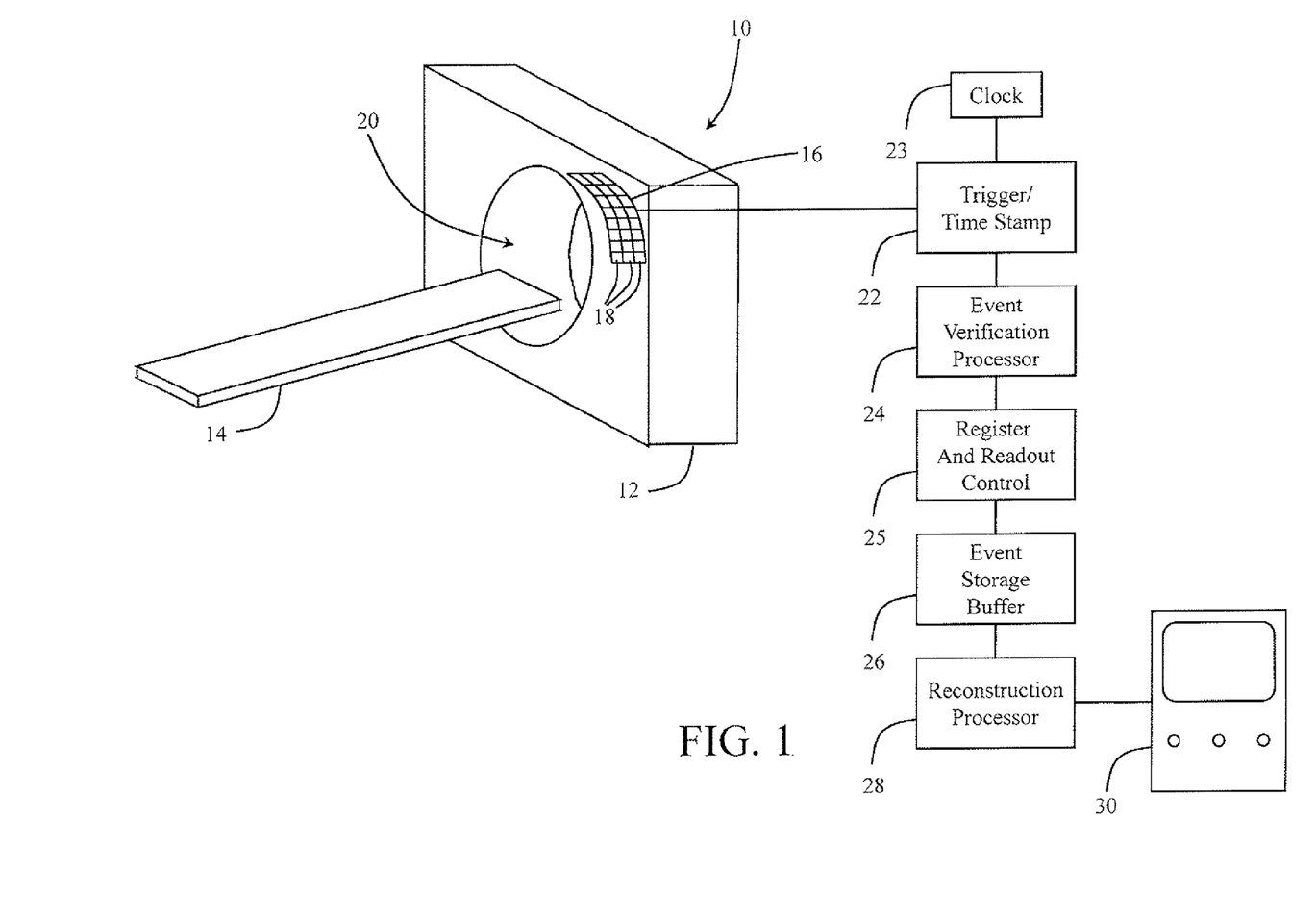
FIG. 1 is a diagrammatic illustration of a nuclear imaging device in accordance with the present application.

With reference to FIG. 1, a diagnostic imaging device 10 includes a housing 12 and a subject support 14. Enclosed within the housing 12 is a detector array 16. The detector array 16 includes a plurality of individual detector elements 18. While one particular embodiment is described with reference to a positron emission tomography (PET) scanner, it is to be understood that the present application is also useful in astrophysics, such as in gamma ray telescopes, radiography, security, industrial, and other medical applications, such as single photon emission computed tomography (SPECT) and x-ray. Generally, the present application finds use in imaging x-rays, gamma rays, or other charged particles with high energy and spatial resolution. The array 16 is arranged so that detector elements 18 are disposed adjacent an imaging region 20. The detector array 16 can be a ring of detectors 18, multiple rings, one or more discrete flat or arced panels, or the like. In positron emission tomography (PET), pairs of gamma rays are produced by a positron annihilation event in the imaging region and travel in opposite directions. These gamma rays are detected as pairs, with a slight time difference (on the order of nanoseconds) between detections if one gamma ray travels farther to reach a detector than the other. Accordingly, in PET scanners, the detector arrays typically encircle the imaging region.

Before the PET scan commences, a subject is injected with a radiopharmaceutical. In one common exam, the radiopharmaceutical contains a radioactive element coupled to a tag molecule. The tag molecule is associated with the region to be imaged, and tends to gather there through normal body processes. For example, rapidly multiplying cancer cells tend to expend abnormally high amounts of energy duplicating themselves. So, the radiopharmaceutical can be linked to a molecule, such as glucose that a cell typically metabolizes to create energy, gather in such regions and appear as "hot spots" in the image. Other techniques monitor tagged molecules flowing in the circulatory system.

When a gamma ray strikes the detector array 16, a time signal is generated. A triggering processor 22 monitors each detector 18 for an energy spike, e.g., integrated area under the pulse, characteristic of the energy of the gamma rays generated by the radiopharmaceutical. The triggering processor 22 checks a clock 23 and stamps each detected gamma ray with a time of leading edge receipt stamp. The time stamp, energy estimate and position estimation is first used by an event verification processor 24 to determine if the hit data can be used for a subsequent coincidence check. Accepted pairs define a lines of response (LORs). Because gamma rays travel at the speed of light, if detected gamma rays arrive more than several nanoseconds apart, they probably were not generated by the same annihilation event and are discarded. Timing is especially important in time of flight PET (TOF-PET), as the minute difference in substantially simultaneous events can be used to further localize the annihilation event along the LOR. As the temporal resolution of events becomes more precise, the higher the accuracy with which an event can be localized along its LOR. After events have been time stamped and verified, they are passed to a register and readout control 25.

LORs are stored in an event storage buffer 26, and a reconstruction processor 28 reconstructs the LORs into an image representation of the subject using filtered backprojection or other appropriate reconstruction algorithm. The reconstruction can then be displayed for a user on a display device 30, printed, saved for later use, and the like.

In one embodiment, a flash TDC is used. The TDC includes a linear feedback shift register (LFSR) for coarse time binning, and a cascaded delay logged loop (DLL) for fine time binning. The DLL is logged to an external reference frequency that controls all TDCs of the system. This offers fast time to digital conversion with low dead times. Timestamp values greater than $10^8$ counts/second can be achieved. Incoming signals for PET imaging normally operate at about $10^3$ counts/second, (e.g., for $F_{18}$ studies) and normally do not exceed $10^4$ counts/second for high count rate studies, using 4×4 $mm^2$ detector elements. With such a surplus of timestamping potential available, TDCs can be multitasked to monitor several detector elements without sacrificing data.

Figure 2:
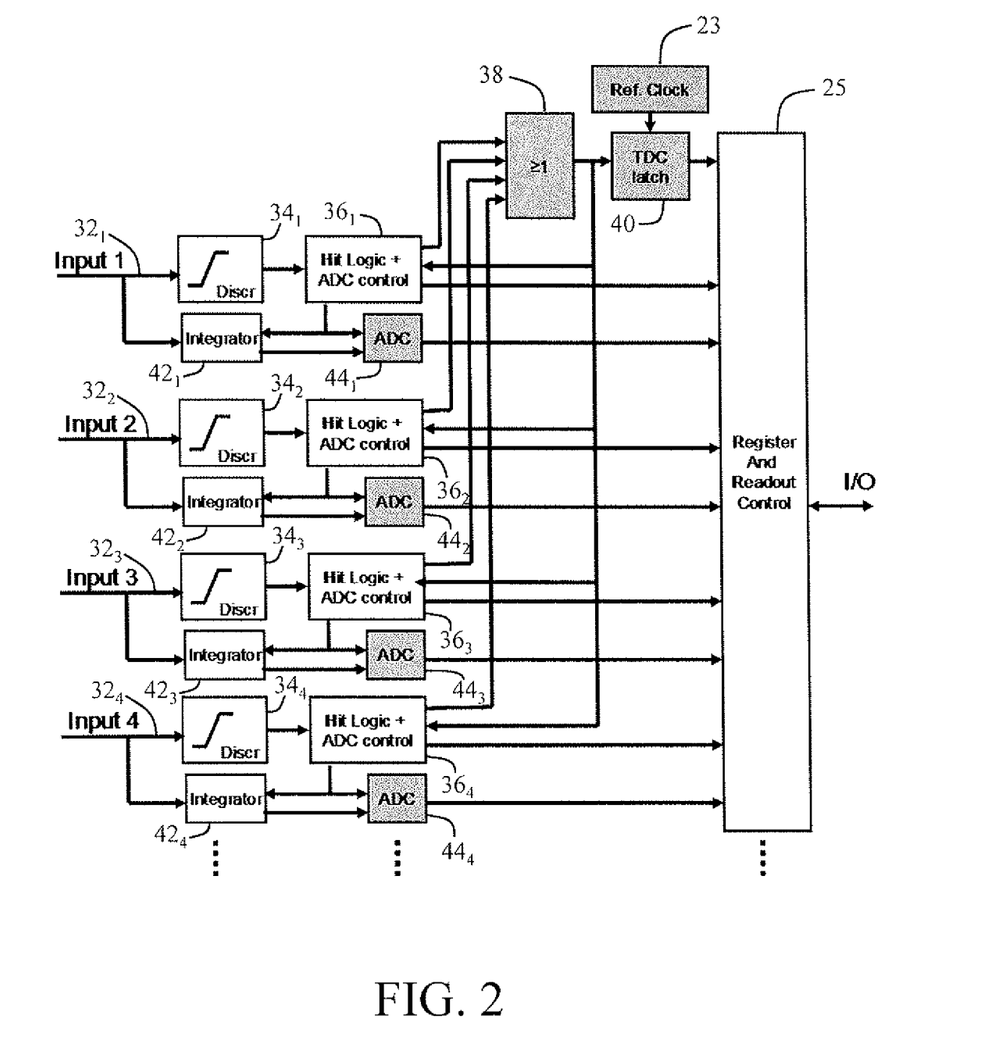
FIG. 2 is a flow diagram of a triggering process where several input channels are encoded together for timestamping purposes.

By using a common digital OR signal, several detector elements that are spatially dispersed are processed by a single TDC. With reference to FIG. 2, a portion of the triggering circuitry is shown. Several input channels $32_1, 32_2, 32_3, 32_4$ from individual detector elements feed into respective leading edge detectors $34_1, 34_2, 34_3, 34_4$. When a leading edge is detected, combined hit logic and ADC controllers $36_1, 36_2, 36_3, 36_4$ determine whether the detected leading edge was a valid event hit. If the leading edge is determined to be a valid hit, the hit logic/ADC controller $36_1, 36_2, 36_3, 36_4$ sends a signal to the register and readout control 25, which identifies the channel $32_1, 32_2, 32_3, 32_4$. The hit logic $36_1, 36_2, 36_3, 36_4$ also temporarily latches down to prevent processing of further hits until the current hit is processed and read out. At the same time it sends the signal to an encoding unit 38 where the hit signals are digitally ORed. The output latches a TDC 40 to timestamp the event. Still simultaneously, the hit logic/ADC controller $36_1, 36_2, 36_3, 36_4$ sends a signal to an integrator $42_1, 42_2, 42_3, 42_4$. Upon receipt of that signal, the integrator $42_1, 42_2, 42_3, 42_4$ determines an analog energy value of the detected event. An ADC $44_1, 44_2, 44_3, 44_4$ then converts the energy value to a digital energy value and sends it along to the register and readout control 25. The register and readout control 25 then outputs the digital amplitude, location (radiation receiving detector,) and digital time stamp for each detected event. When the ADC completes the conversion and the data is read out, the hit logic $36_1, 36_2, 36_3, 36_4$ unlatches and opens the input channels $32_1$, $32_2$, $32_3$, $32_4$ to detect further events. In the above described embodiment, consumed power is reduced by almost a factor of 4.

With continuing reference to FIG. 2, four input channels $32_1$, $32_2$, $32_3$, $32_4$ are shown. It is to be understood that more or fewer channels $32_1$, $32_2$, $32_3$, $32_4$ can be tied to a single TDC 40. The depicted embodiment makes efficient use of resources, as the TDCs 40 are responsible for approximately 90% of the power consumption. The reason for such marked power consumption is the demand for very small time bins with small jitter (<50 ps). By combining the time to digital conversion operation for several detector elements with a digital OR trigger decreases the actual number of TDCs 40 needed (by a factor of 4 in the embodiment of FIG. 2.) As the remaining TDC channels become smaller and faster, a greater than propionate energy reduction is possible. For example, if the TDCs are reduced by a factor of 4-8, an energy reduction by about a factor of 5-10 is possible while improving the time stamping performance. This allows a high end pixelated readout while consuming a relatively low amount of power (approximately 0.1 W/cm$^2$.) With this arrangement, an entire whole body PET detector can be driven with a few hundred Watts. The cooling system can be simplified, and temperature sensitive parts can be regulated with greater ease. Also, the power supply effort can be dramatically reduced for low voltage devices.

Figure 3:
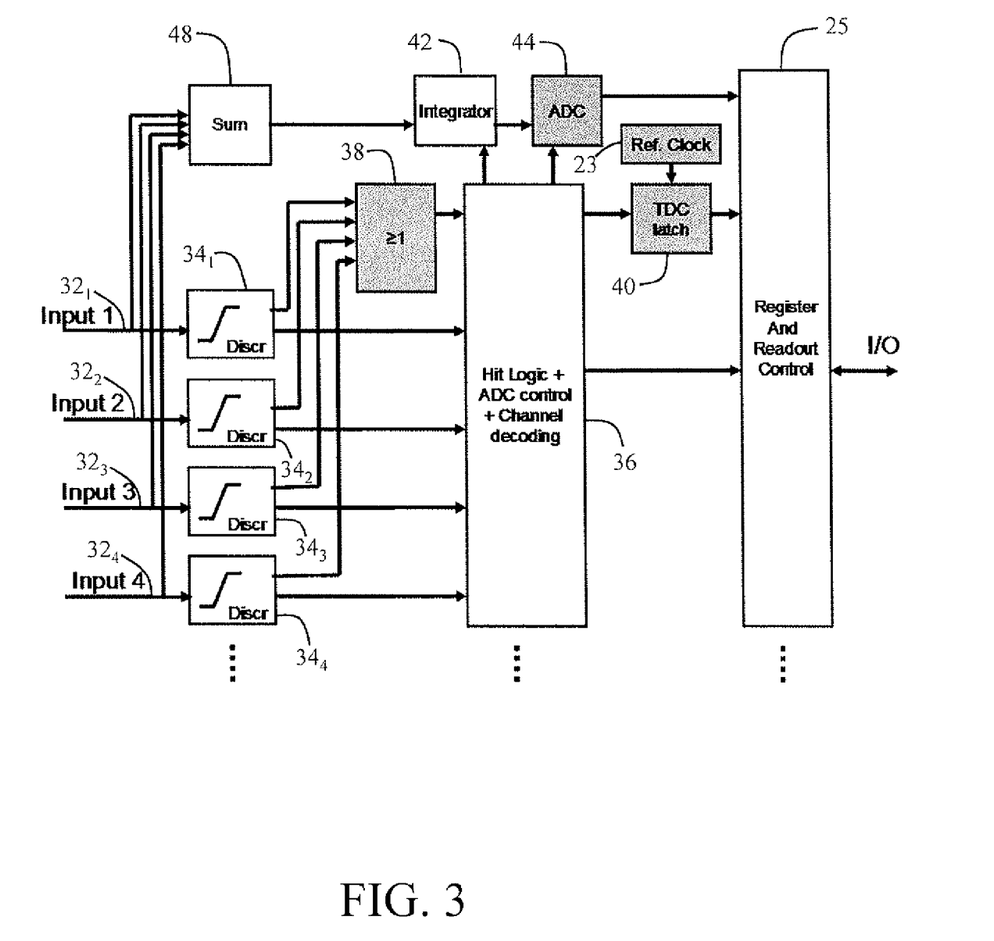
FIG. 3 depicts another embodiment of the triggering process where summing, integrating, and analog-to-digital conversion are encoded for several input channels.

In another embodiment, as shown in FIG. 3, additional components have been combined to further simplify and reduce power consumption of the detector. As in the previous embodiment, several input channels $32_1$, $32_2$, $32_3$, $32_4$ from individual detector elements feed into respective leading edge detectors $34_1$, $34_2$, $34_3$, $34_4$. The input channels $32_1$, $32_2$, $32_3$, $32_4$ are summed together by a summation processor 48 and processed by a single integrator 42. Again, the inputs $32_1$, $32_2$, $32_3$, $32_4$ are from non-contiguous detectors, because typically, only one of the inputs is responding to a hit and the others are substantially zero, the integrated sum represents the energy of the one detected hit. A logic processor 36 determines whether the hit is valid, and which channel fired. If the hit is valid, the integrated signal is processed by an ADC 44. As in the previous embodiment, the corresponding hit logic $36_1$, $36_2$, $36_3$, $36_4$ temporarily latches down when a hit is detected. This allows both the necessary chip area for the circuit layout and the power to be reduced. The signal is time stamped by a TDC 40. The location of the hit detector, the digital amplitude or energy of the hit and the time stamp for the hit pass to register and readout control 25.

For the embodiment of FIG. 3, channel dead time is determined by four times the analog to digital conversion time. For a 10 bit successive approximation conversion, this dead time is approximately 1 μs, which for 10$^4$ counts/second equates to about 1% dead time. This embodiment also provides a generally acceptable signal to noise ratio despite summing the noise of several detector channels. For both this and the previous embodiments it is generally true that the power savings is greater than the encoding ratio used. This is because the TDCs can be embodied on a substantially smaller geometry. This reduces the capacitive load. Also, buffers and latches can also be designed to be smaller, faster, and can be driven with lower power.

Figure 4:
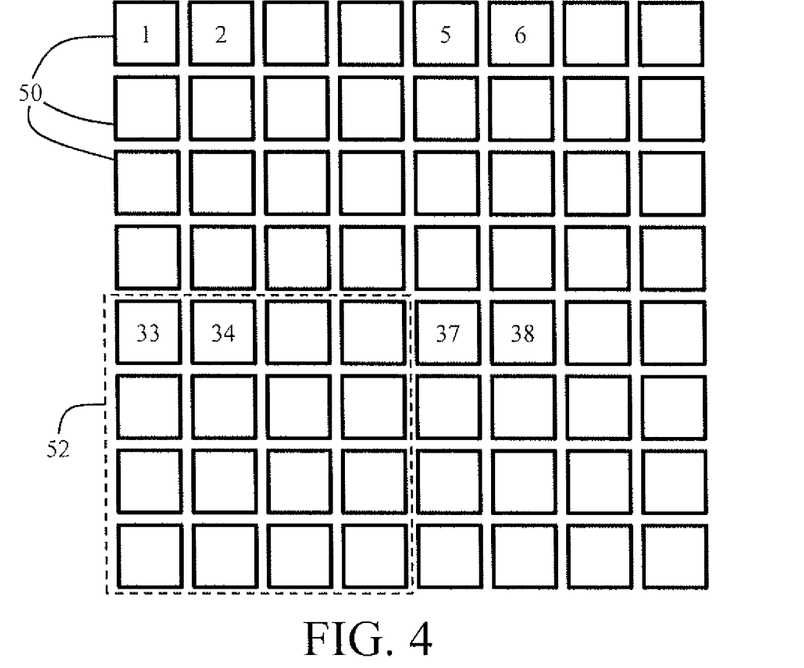
FIG. 4 depicts a possible channel encoding scheme.

With the two previously described embodiments, energy consuming components are more effectively used. In order to multitask these components to multiple channels, the combined channels are physically mapped in such a way to avoid cross-talk. As scintillation events caused by incoming gamma events can be scattered over several pixels, it is undesirable to map adjacent channels together into a single OR trigger. In one embodiment, the channels are physically spread apart from each other. With reference to FIG. 4, a section of 8×8 individual detectors 50 are shown. Although square detectors are shown, any shape of detector could also be used, such as hexagonal, round, rectangular or others. As mentioned previously, any number can be used for the encoding, 4:1 was illustrated in FIGS. 2 and 3, and is realized by using 2×2 sub-blocks. Another convenient ratio is 9:1 realized by using 3×3 sub-blocks. Non-square arrangements are also possible, such as 8:1, by using 2×4 sub blocks. In a 3:1 encoding of hexagonal detectors, it is possible to use sub-groups of 7 or 19 detectors, arranged in a ring.

Figure 5:
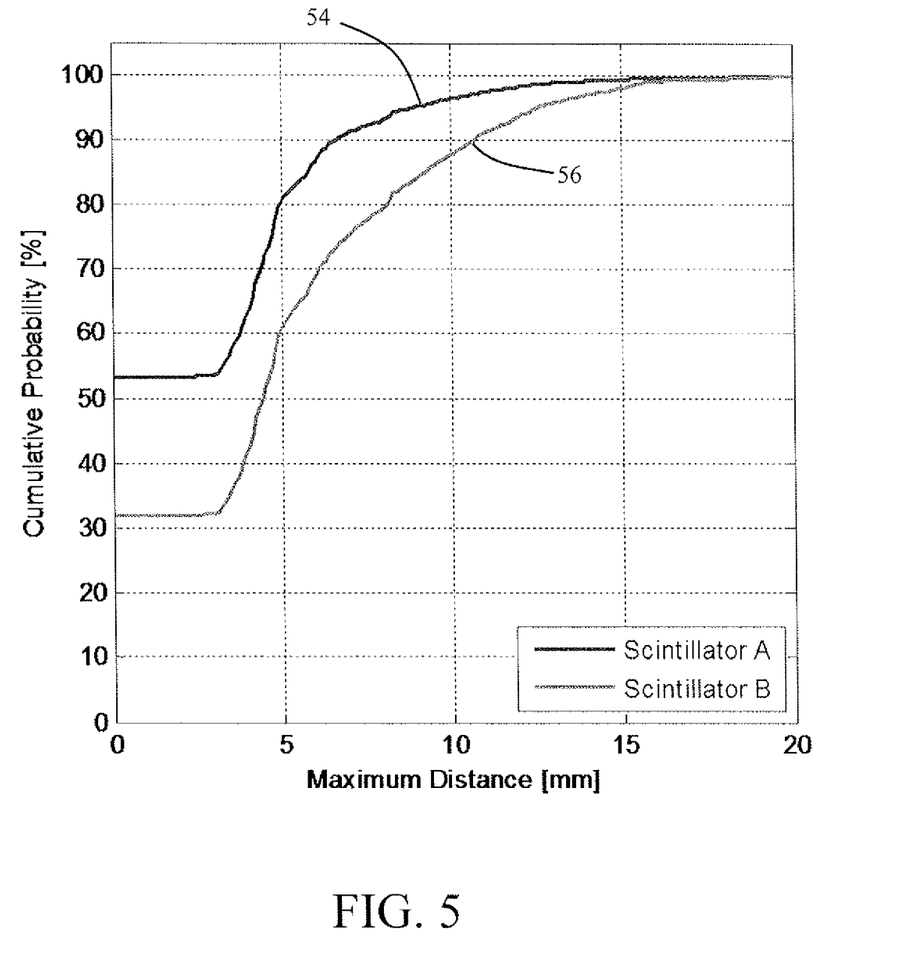
FIG. 5 is a graph that depicts a probability of non-correlation of events as a function of distance between detector elements that are encoded together.

In the embodiment of FIG. 4, the array is divided into four 1:4 sub blocks 52. The pixels labeled 1, 5, 33, and 37 are wired together to form the inputs $32_1$, $32_2$, $32_3$, $32_4$ of the circuits of FIG. 2 or 3. Similarly, the pixels labeled 2, 6, 34, and, 38 are connected, and so on. The grouping of the pixels is selected to minimize the possibility of two or more detectors detecting the same event. With reference to FIG. 5, in a pixelated detector using 4×4 mm detector elements, the probability of non-correlation of detectors is mapped for two PET scintillators 54 and 56 as a function of the distance between the detectors. With a spread of 16 mm, approximately 99% of events for both scintillators will be uncorrelated.

Figure 6:
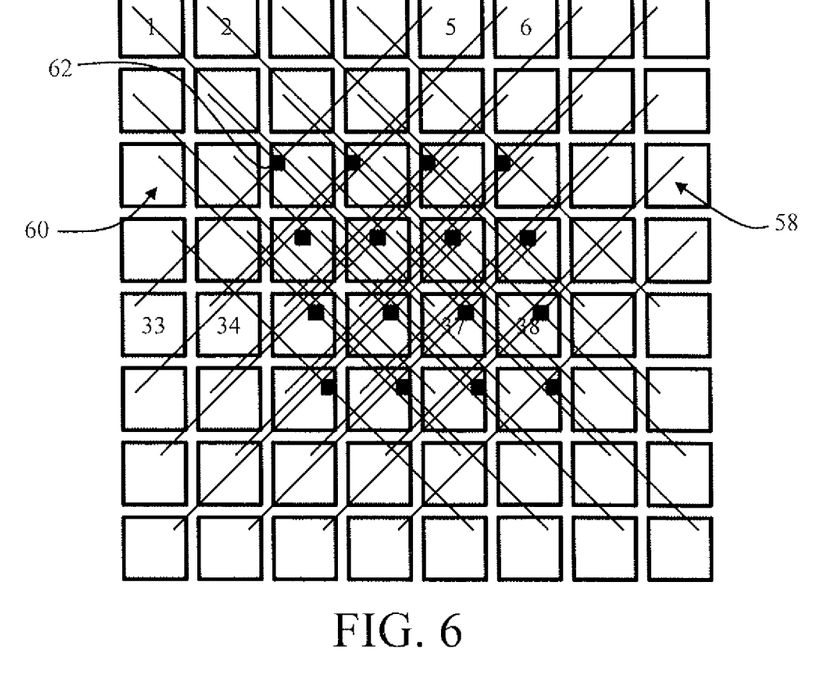
FIG. 6 depicts a possible circuit board wiring layout for the encoding scheme of FIG. 4.

Although the distribution of connected channels could theoretically be random, with the constraint of at least a four pixel separation, it is convenient to arrange the connected pixels in such a way that will allow for ease of wiring. With reference now to FIG. 6, a possible wiring scheme for an 8×8 grid of detectors with a 4:1 encoding ratio is depicted. The circuit board is wired in two parallel planes, such as on both sides of a typical printed circuit board. In the first plane, one set of wirings 58 runs in one direction (from southwest to northeast in FIG. 6), while a second set 60 runs in the second plane in a second direction (from northwest to southeast). Each wiring contacts two pixels and is connected to a counterpart wiring at a quad connection point, which bridges the gap between the parallel wiring planes. So in FIG. 6, pixels 5 and 33 are connected by a wire from the first set 58 and pixels 1 and 37 are connected by a wire from the second set 60. The two wires are connected at a quad connection point 62. FIG. 6 provides one convenient way to condense wiring for the 64 pixel array into 16 quad channels. Other wiring schemes are certainly possible.

Figure 7:
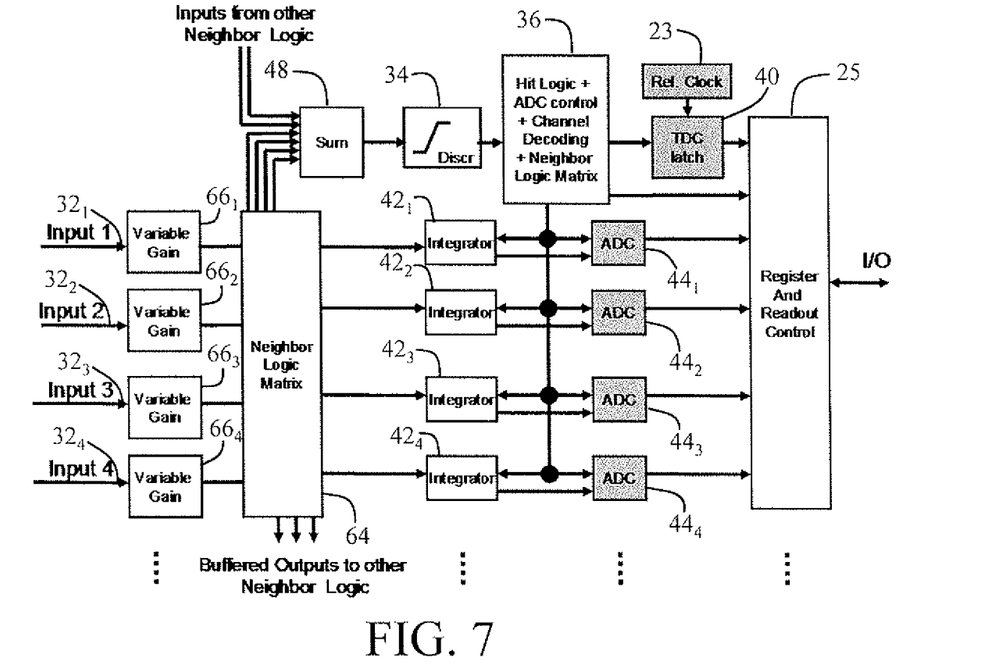
FIG. 7 introduces the use of neighbor logic to a channel encoding scheme.

Neighbor logic can be used if pixel pitch and detector pitch are not identical, and also for power savings of the above-mentioned embodiments. The neighbor logic can be overlapping or non-overlapping to neighboring detectors. With reference to FIG. 7, like reference numerals indicate like components with FIGS. 2 and 3. A variable neighbor logic matrix 64 selects which of channels $32_1$, $32_2$, $32_3$, $32_4$ are going to be summed by the summer 48 for use as a timing channel. One embodiment is based on a switch matrix. If the hit logic and ADC controller 36 determines that a discriminator threshold of the signal sum is exceeded, a time stamp is generated by the TDC 40 and integration and digitization of the signals used is performed by the respective integrator 42 and ADCs 44. The time stamp for the summed signal is used, so gain and delay matching of the input signals is important to know. In one embodiment, the neighbor logic matrix 64 includes transistors, a variable gain adjustment for the sum can be implemented by local DACs $66_1$, $66_2$, $66_3$, $66_4$ that control the input impedance without adding a variable delay. A delay match can be realized externally by using a layout with a constant and almost equivalent signal path length. In an embodiment that includes MA-PMTs, a dynode signal can be fed into the sum, obviating a need for further delay matching.

For SiPM array readout, small time differences can be adjusted by the gain due to a slower impulse response of the devices. For example, for a 30 ns rise time, a time delay shift of 30 ps/gain % is achievable. The value of the threshold signal can be adjusted to reject more or fewer events as is desired.

Figure 8:
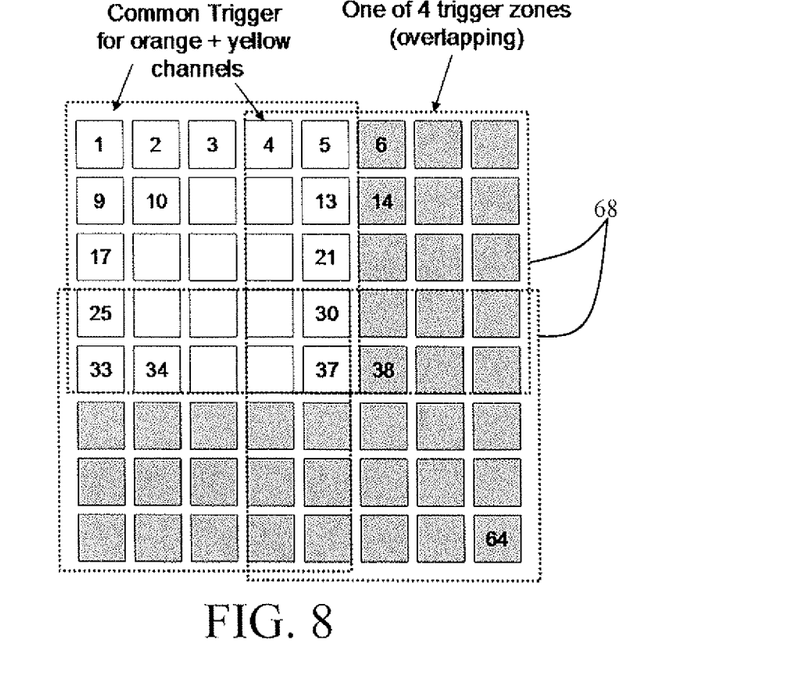
FIG. 8 depicts possible overlapping triggering zones for implementation of the neighbor logic of FIG. 7.

FIG. 8 shows a section of a detector with overlapping trigger zones 68. the detectors marked 5, 13, 21, 30, 33, 34, 35, 36, and 37 are contained within multiple trigger zones. The detector setup of FIG. 8 implemented with the neighbor logic of FIG. 7 uses four TDCs 40 and sixty-four ADCs 44. As the TDC 40 consumes most of the power of the TDC/ADC, the power savings scales with the trigger zone size. Therefore, the greater the trigger zone size, the greater the power savings, but pile-up and dead time effects also scale with the trigger zone size. For larger trigger zones it is possible to use ADCs 44 that allow on-chip energy thresholding to reject baseline hits to reduce the amount of data to be transferred. In one embodiment, the DACs 66 could be ramped with a lower energy threshold as a starting value. In the above described embodiment, the power is reduced by almost a factor of 16.

Figure 9:
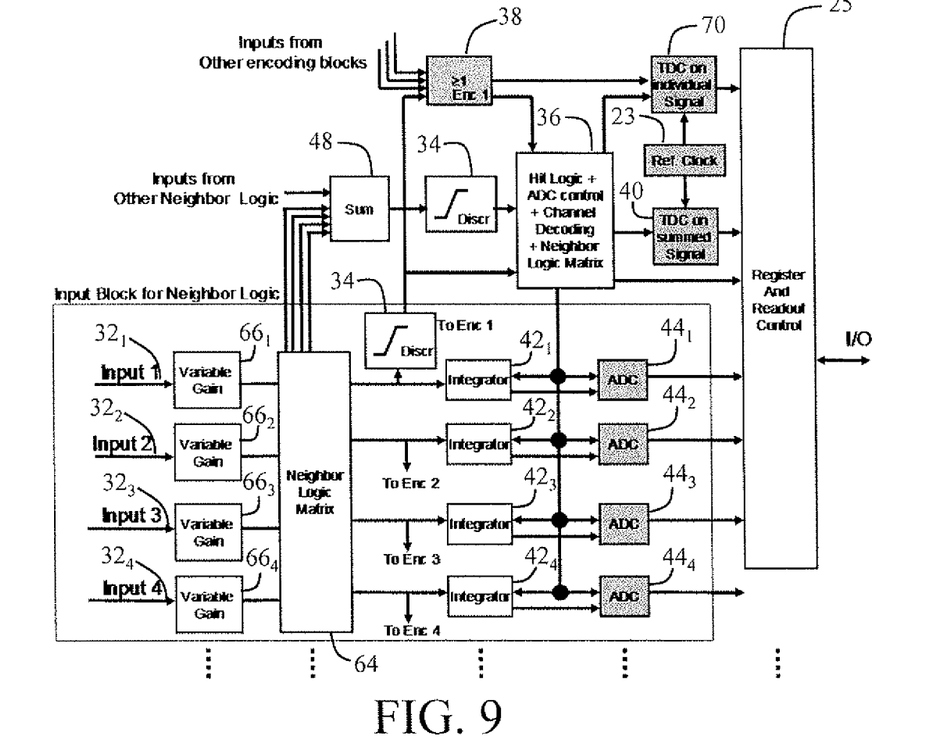
FIG. 9 introduces a combination of individual trigger zone time stamping as a replacement or supplement to time stamping on a summed signal.
Figure 10:
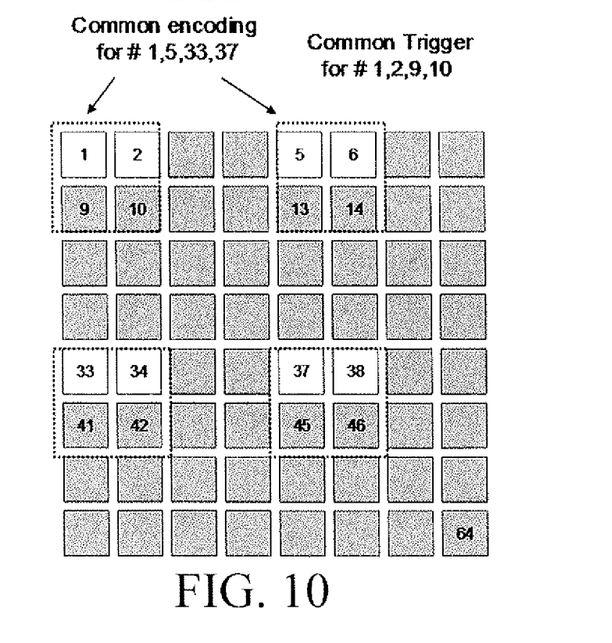
FIG. 10 introduces discrete triggering zones to the encoding scheme of FIG. 4.

In another embodiment, as shown in FIG. 9, an additional TDC value is added for each incoming signal. In the depicted embodiment, the encoding unit 38 that uses the OR trigger passes the individual signal on to an individual signal TDC 70. This embodiment provides individual time stamps for each signal coming from a zone exceeding the lower trigger threshold. No exact gain and delay matching is needed, as the TDC value on the summed signal (coming from the TDC) is optional and time stamping can be realized by weighting the individual timestamps of the zone. The trigger threshold on the summed signal can be relatively high to reject scattered events. The encoding zones are defined as discussed previously, with sufficiently disparate physical correlation. FIG. 10 depicts an encoding scheme similar to that of FIG. 4, and adds smaller triggering zones 68 than in FIG. 8. Such an embodiment of 64 detectors would use 16 TDCs 70 for 16 triggering zones 68 (with a TDC 40 on the sum being optional) and 64 ADCs 44.

Referring again to FIGS. 9 and 10, if a summed trigger of a zone 68 exceeds the threshold (e.g. detectors marked 1, 2, 9, and 10) the corresponding integrators $42_1$, $42_2$, $42_3$, $42_4$ and ADCs $44_1$, $44_2$, $44_3$, $44_4$ are started and the corresponding TDC values are latched. Here, the pixels 1, 5, 33, and 37 feed one ORed TDC 40, the pixels 2, 6, 34, and 38 feed another TDC 40, and so on. The corresponding TDC values are transferred to the readout controller 25 together with the channel ID of which channel fires. Alternatively, the timestamp value of the summed signal can also be stored. In the above described embodiment, the power is reduced by almost a factor of 8. This embodiment uses slightly more power, but no exact gain and delay matching is required. Individual TDC and ADC values are provided within the trigger zone for ToF timestamping and allowing Anger logic based pixel identification by providing at least four neighboring detector values.

Figure 11:
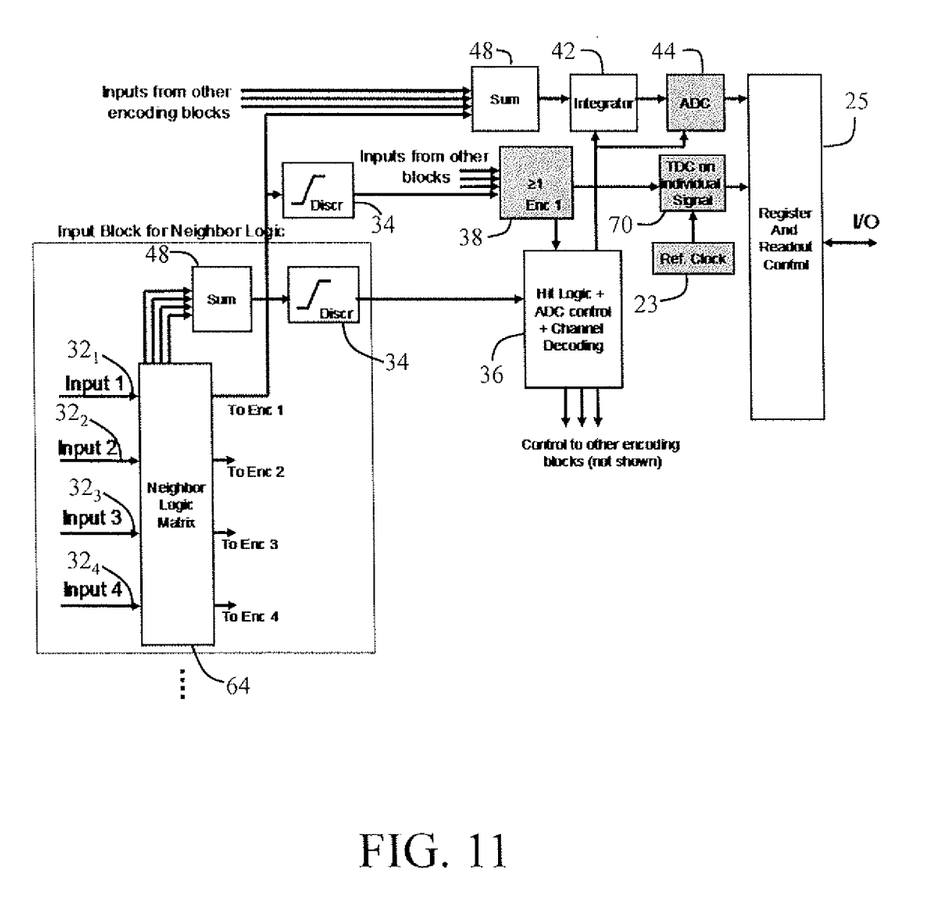
FIG. 11 combines both ADC and TDC encoding with neighbor logic.

With reference now to FIG. 11, another embodiment is shown. If the ADC encoding is chosen to be similar to the TDC encoding, further chip area and power can be saved while maintaining the trigger zone readout. Based on the pixel mapping, the number of TDCs 40 and ADCs 44 required to perform the task scales with the encoding ratio. In this embodiment, a 4:1 encoding is shown, which uses 16 TDCs 40 and 16 ADCs 44 for 64 input channels 32 (detector pixels) while guaranteeing energy and timestamp values for each trigger zone (68 in FIG. 10). This embodiment uses the analog sum of several detector inputs for the energy channel. The ADC encoding leads to a lower number of necessary ADCs.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A diagnostic imaging device comprising:
    a signal processing circuit which processes hit signals from a detector array which detects radiation from an imaging region, the hit signals being indicative of a corresponding detector being hit by a radiation photon, the signal processing circuit including:
        a plurality of input channels, each input channel receiving hit signals from a corresponding detector element such that each input channel corresponds to a location at which each hit signal is received;
        summers that each sum hit signals from a subset of the plurality of input channels;
        a plurality of integrators, each integrator integrating signals from the the summer of one of the subsets to determine an energy value associated with each radiation hit;
        a plurality of analog-to-digital converters (ADCs) for converting the integrated energy value into a digital energy value, there being one ADC for each subset of input channels;
        a plurality of time to digital converters (TDCs) that receive the hit signals and generate a digital time stamps, the ADCs and TDCs being in a 1:1 ratio;
        OR logic that relays signal hits from the subset of the plurality of input channels to the ADC and one of the time to digital converters, the subset including more than one input channel such that more than one input channel is connected with each ADC and/or each time-to-digital converter;
        a register and read out which reads out the locations, the digital energy values, and the digital time stamps for hit signals.

2. The diagnostic imaging device as set forth in claim 1, further including:
    an event verification processor that applies verification criteria to detector channel hits;
    an event storage buffer for storing valid time stamped events; and
    a reconstruction processor for reconstructing valid events into an image representation of a subject in the imaging region.

3. The diagnostic imaging device as set forth in claim 1, wherein the
    summer sums a pre-selected number of detector channel inputs according to an encoding ratio before the integrator integrates the energy values.

4. The diagnostic imaging device as set forth in claim 1, wherein the subset of the plurality of input channels includes individual input channels that are connected to detectors which are physically separated from each other.

5. The diagnostic imaging device as set forth in claim 4, wherein the individual input channels are spaced at least two pixels apart from each other.

6. The diagnostic imaging device as set forth in claim 1, wherein the signal processing circuit further includes a circuit board that includes wiring in at least a first plane and a second plane parallel to the first plane.

7. A diagnostic imaging device comprising:
a signal processing circuit which processes hit signals from a detector array which detects radiation from an imaging region, the hit signals being indicative of a corresponding detector being hit by a radiation photon, the signal processing circuit including:
   a plurality of input channels, each input channel receiving hit signals from a corresponding detector element such that each input channel corresponds to a location at which each hit signal is received;
   a plurality of integrators for integrating signals from the input channels to determine an energy value associated with each hit;
   a plurality of analog-to-digital converters (ADCs) for converting the integrated energy value into a digital energy value;
   a plurality of time to digital converters (TDCs) that receive the hit signals and generate a digital time stamp;
   OR logic that relays signal hits from a subset of the plurality of input channels to one of the ADC and one of the time to digital converters, the subset including more than one input channel such that more than one input channel is connected with each ADC and/or each time-to-digital converter;
   a register and read out which reads out the locations, the digital energy values, and the digital time stamps for hit signals;
wherein the detector array further includes:
   a neighbor logic matrix that receives hit signals from the input channels and selects channels to be combined to create a timing signal to be conveyed to one of the time-to-digital converters to generate the time stamp.

8. The diagnostic imaging device as set forth in claim 7, wherein the detector array further includes:
   a plurality of variable gain and time matching circuits to adjust the hit signals on the plurality of inputs before the hit signals are analyzed by the neighbor logic matrix.

9. The diagnostic imaging device as set forth in claim 7, wherein the detector array further includes:
   a plurality of trigger zones, each trigger zone encompassing a plurality of input channels, any one of the input channels capable of starting a summing operation for the entire trigger zone upon receiving an event hit.

10. The diagnostic imaging device as set forth in claim 9, wherein at least one of the plurality of input channels is included in more than one trigger zone.

11. The diagnostic imaging device as set forth in claim 7, wherein there is one ADC for each input channel and a single TDC for a plurality of input channels.

12. The diagnostic imaging device as set forth in claim 7, wherein the detector array further includes:
   a plurality of time-to-digital converters that time stamp individual signals from an encoding block in addition to the time-to-digital converters that time stamp summed signals.

13. The diagnostic imaging device as set forth in claim 7, wherein the signal processing circuit further includes a summer that sums a plurality of input channels and there is one ADC for the plurality of input channels and the ADCs, the integrators, and TDCs are in a 1:1 ratio.

14. A method of diagnostic imaging comprising:
processing signals from a detector array that detects radiation from an imaging region, the signals being indicative of a corresponding detector being hit by a radiation photon;
receiving hit signals from a plurality of input channels, each input channel having a corresponding detector element such that each input channel corresponds to a location at which each hit signal is received;
integrating signals from the input channels to determine an energy value associated with each radiation hit;
summing a plurality of input channels for relay to one ADC;
converting the integrated energy value into a digital energy value by one of a plurality of analog-to-digital converters (ADCs);
receiving the hit signals and generating a digital time stamp by one of a plurality of time-to-digital converters (TDCs);
relaying signal hits from a subset of the plurality of input channels to one of the ADC and one of the time to digital converters, the subset including more than one input channel such that more than one input channel is connected with each ADC and/or each time-to-digital converter; and
reading out the locations, the digital energy values, and the digital time stamps for hit signals.

15. A method of diagnostic imaging, comprising:
processing signals from a detector array that detects radiation from an imaging region, the signals being indicative of a corresponding detector being hit by a radiation photon;
receiving hit signals from a plurality of input channels, each input channel having a corresponding detector element such that each input channel corresponds to a location at which each hit signal is received;
comparing signals from the input channels with a neighbor logic matrix and determining which of the signals will be passed on for a summation operation;
integrating signals from the input channels to determine an energy value associated with each radiation hit;
converting the integrated energy value into a digital energy value by one of a plurality of analog-to-digital converters (ADCs);
receiving the hit signals and generating a digital time stamp by one of a plurality of time-to-digital converters (TDCs); and
reading out the locations, the digital energy values, and the digital time stamps for hit signals.

16. The method as set forth in claim 15, wherein there is one ADC for each input channel and a single TDC for a plurality of input channels.

17. The method as set forth in claim 15, wherein there is one ADC for each input channel and a single TDC for a plurality of input channels.

18. The method as set forth in claim 15, wherein individual signals from an encoding block are time stamped by a plurality of time-to-digital converters, in addition to time stamping summed signals.

19. The method as set forth in claim 15, summing a plurality of input channels, where there is one ADC for the plurality of input channels and the ADCs, the integrators, and TDCs are in a 1:1 ratio.

* * * * *